United States Patent
Findley et al.

(10) Patent No.: US 9,737,442 B2
(45) Date of Patent: Aug. 22, 2017

(54) METHOD AND APPARATUS FOR APPLYING ELASTIC PARTS UNDER TENSION TO AN ADVANCING CARRIER

(71) Applicant: The Procter & Gamble Company, Cincinnati, OH (US)

(72) Inventors: Daniel Patrick Findley, Finneytown, OH (US); Joseph Allen Eckstein, Sunman, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/168,655

(22) Filed: May 31, 2016

(65) Prior Publication Data
US 2016/0354258 A1 Dec. 8, 2016

Related U.S. Application Data

(60) Provisional application No. 62/169,703, filed on Jun. 2, 2015.

(51) Int. Cl.
*B65G 47/244* (2006.01)
*A61F 13/00* (2006.01)
(Continued)

(52) U.S. Cl.
CPC .. *A61F 13/15764* (2013.01); *A61F 13/15593* (2013.01); *B65G 29/00* (2013.01);
(Continued)

(58) Field of Classification Search
CPC .............. A61F 13/15764; B65H 35/08; B65H 2801/57; B65H 2301/332; B65G 47/848;
(Continued)

(56) References Cited

U.S. PATENT DOCUMENTS 2,075,189 A 10/1935 Galligan et al
3,025,199 A 6/1956 Harwood
(Continued)

FOREIGN PATENT DOCUMENTS

EP 2 554 143 A1 2/2013

OTHER PUBLICATIONS

PCT International Search Report dated Aug. 19, 2016, 10 pages.

*Primary Examiner* — Mark A Deuble
(74) *Attorney, Agent, or Firm* — Charles R. Matson

(57) ABSTRACT

The present disclosure relates to assembling, advancing, reorienting, and/or transferring stretched elastic parts during the assembly of absorbent articles. As described herein, a transfer assembly reorients a stretched elastic part from a first orientation, wherein the direction of stretch is generally parallel to the machine direction, to a second orientation, wherein the direction of stretch is generally perpendicular to the machine direction. The reoriented elastic part is then transferred to a carrier while maintaining the stretched condition of the elastic part. The orientation and/or configuration of vacuum apertures in a carrier surface relative to the direction of stretch of the elastic part and relative to the machine direction helps to prevent the elastic part from contracting, while at the same time helps to allow the elastic part to slide off the carrier surface without snagging and/or sticking to aperture perimeter edges.

17 Claims, 15 Drawing Sheets

(51) Int. Cl.
*A61F 13/15* (2006.01)
*B65G 47/91* (2006.01)
*B65G 29/00* (2006.01)
*B65G 47/00* (2006.01)
*B65G 47/84* (2006.01)
*B65H 35/08* (2006.01)

(52) U.S. Cl.
CPC ............ *B65G 47/00* (2013.01); *B65G 47/244* (2013.01); *B65G 47/848* (2013.01); *B65G 47/915* (2013.01); *B65H 35/08* (2013.01); *B65G 2201/022* (2013.01); *B65H 2301/332* (2013.01); *B65H 2801/57* (2013.01)

(58) Field of Classification Search
CPC ............ B65G 2201/022; B65G 47/915; B65G 47/244
USPC .......................................... 198/377.04, 377.08
See application file for complete search history.

(56) References Cited

U.S. PATENT DOCUMENTS

| | | | |
|---|---|---|---|
| 3,215,250 A * | 11/1965 | Schubert | A24C 5/336 198/377.04 |
| 3,319,764 A * | 5/1967 | Gamberini | A24C 5/336 198/377.04 |
| 3,848,594 A | 11/1974 | Buell | |
| 3,860,003 A | 1/1975 | Buell | |
| 3,952,865 A * | 4/1976 | Rudszinat | A24C 5/326 198/377.04 |
| 4,107,364 A | 8/1978 | Sisson | |
| 4,209,563 A | 6/1980 | Sisson | |
| 4,515,595 A | 5/1985 | Kievit et al. | |
| 4,610,678 A | 9/1986 | Weisman et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,704,115 A | 11/1987 | Buell | |
| 4,795,454 A | 1/1989 | Dragoo | |
| 4,834,735 A | 5/1989 | Alemany et al. | |
| 4,834,741 A | 5/1989 | Sabee | |
| 4,846,815 A | 7/1989 | Scripps | |
| 4,888,231 A | 12/1989 | Angstadt | |
| 4,894,060 A | 1/1990 | Nestegard | |
| 4,909,803 A | 3/1990 | Aziz et al. | |
| 4,940,464 A | 7/1990 | Van Gompel et al. | |
| 4,946,527 A | 8/1990 | Battrell | |
| 5,025,910 A | 6/1991 | Lasure et al. | |
| 5,092,861 A | 3/1992 | Nomura et al. | |
| 5,151,092 A | 9/1992 | Buell et al. | |
| 5,167,897 A | 12/1992 | Weber et al. | |
| 5,221,274 A | 6/1993 | Buell et al. | |
| 5,224,405 A | 7/1993 | Pohjola | |
| 5,246,433 A | 9/1993 | Hasse et al. | |
| 5,330,458 A | 7/1994 | Buell et al. | |
| 5,360,420 A | 11/1994 | Cook et al. | |
| 5,556,504 A | 9/1996 | Rajala et al. | |
| 5,562,646 A | 10/1996 | Goldman et al. | |
| 5,569,234 A | 10/1996 | Buell et al. | |
| 5,599,335 A | 2/1997 | Goldman et al. | |
| 5,628,097 A | 5/1997 | Benson et al. | |
| 5,643,588 A | 7/1997 | Roe et al. | |
| 5,669,894 A | 9/1997 | Goldman et al. | |
| 5,674,216 A | 10/1997 | Buell et al. | |
| 5,702,551 A | 12/1997 | Huber et al. | |
| 5,735,840 A | 4/1998 | Kline et al. | |
| 5,897,545 A | 4/1999 | Kline et al. | |
| 5,916,661 A | 6/1999 | Benson et al. | |
| 5,928,212 A | 7/1999 | Kline et al. | |
| 5,957,908 A | 9/1999 | Kline et al. | |
| 5,968,025 A | 10/1999 | Roe et al. | |
| 6,107,537 A | 8/2000 | Elder et al. | |
| 6,107,539 A | 8/2000 | Palumbo et al. | |
| 6,116,317 A | 9/2000 | Tharpe, Jr. et al. | |
| 6,118,041 A | 9/2000 | Roe et al. | |
| 6,120,487 A | 9/2000 | Ashton et al. | |
| 6,120,489 A | 9/2000 | Johnson et al. | |
| 6,153,209 A | 11/2000 | Vega et al. | |
| 6,251,097 B1 | 6/2001 | Kline et al. | |
| 6,319,347 B1 | 11/2001 | Rajala et al. | |
| 6,410,129 B2 | 6/2002 | Zhang et al. | |
| 6,426,444 B2 | 7/2002 | Roe et al. | |
| 6,432,098 B1 | 8/2002 | Kline et al. | |
| 6,450,321 B1 | 9/2002 | Blumenthal et al. | |
| 6,545,197 B1 | 4/2003 | Muller et al. | |
| 6,586,652 B1 | 7/2003 | Roe et al. | |
| 6,604,623 B2 | 8/2003 | Sumi et al. | |
| 6,617,016 B2 | 9/2003 | Zhang et al. | |
| 6,627,787 B1 | 9/2003 | Roe et al. | |
| 6,669,618 B2 | 12/2003 | Reising et al. | |
| 6,722,494 B2 | 4/2004 | Nakakado | |
| 6,790,798 B1 | 9/2004 | Suzuki et al. | |
| 6,825,393 B2 | 11/2004 | Roe et al. | |
| 6,861,571 B1 | 3/2005 | Roe et al. | |
| 7,341,087 B2 | 3/2008 | Tabor et al. | |
| 7,371,302 B2 | 5/2008 | Miyamoto et al. | |
| 7,650,984 B2 | 1/2010 | Giuliani et al. | |
| 7,770,712 B2 | 8/2010 | McCabe | |
| 8,636,136 B2 * | 1/2014 | Schoultz | B65G 47/248 156/164 |
| 8,720,666 B2 | 5/2014 | Papsdorf et al. | |
| 8,833,542 B2 * | 9/2014 | Papsdorf | A61F 13/15764 198/377.01 |
| 9,248,053 B2 * | 2/2016 | Ogasawara | A61F 13/15699 |
| 2003/0233082 A1 | 12/2003 | Kline et al. | |
| 2004/0097895 A1 | 5/2004 | Busam et al. | |
| 2004/0158212 A1 | 8/2004 | Ponomarenko et al. | |
| 2007/0078427 A1 | 4/2007 | Raycheck et al. | |
| 2007/0093769 A1 | 4/2007 | Kline et al. | |
| 2009/0312730 A1 | 12/2009 | LaVon et al. | |
| 2010/0012458 A1 * | 1/2010 | Giuliani | B65G 47/244 198/377.04 |
| 2013/0072887 A1 | 3/2013 | LaVon et al. | |
| 2013/0091998 A1 | 4/2013 | Yamamoto et al. | |
| 2013/0211356 A1 | 8/2013 | Nishikawa et al. | |
| 2013/0270069 A1 | 10/2013 | Papsdorf et al. | |
| 2013/0306226 A1 | 11/2013 | Zink et al. | |
| 2014/0005019 A1 | 1/2014 | Hargett et al. | |

* cited by examiner

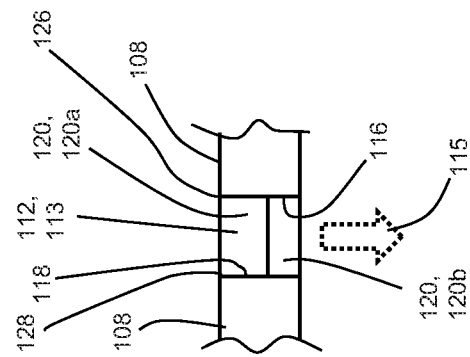
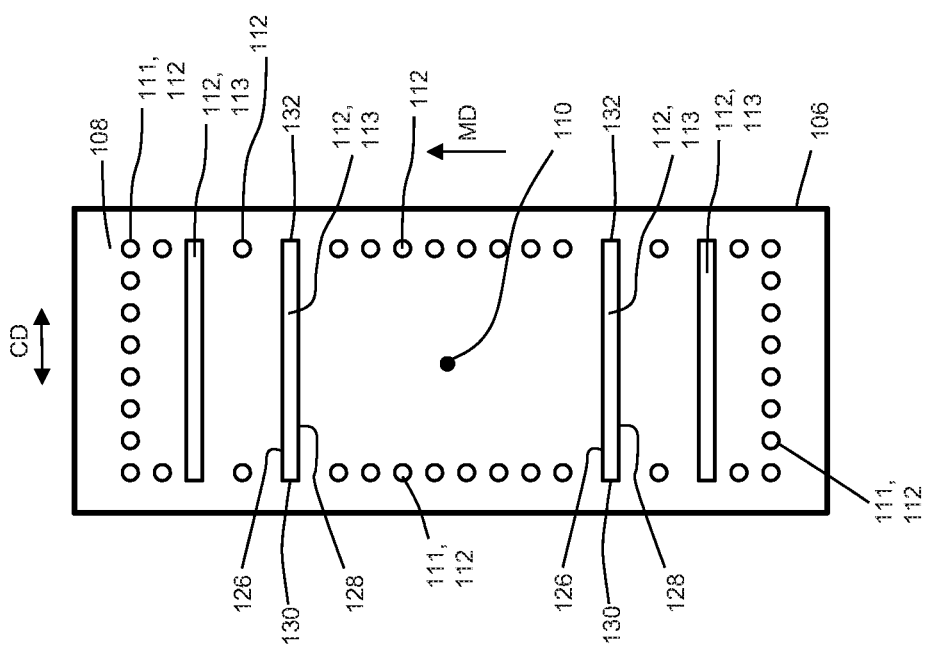

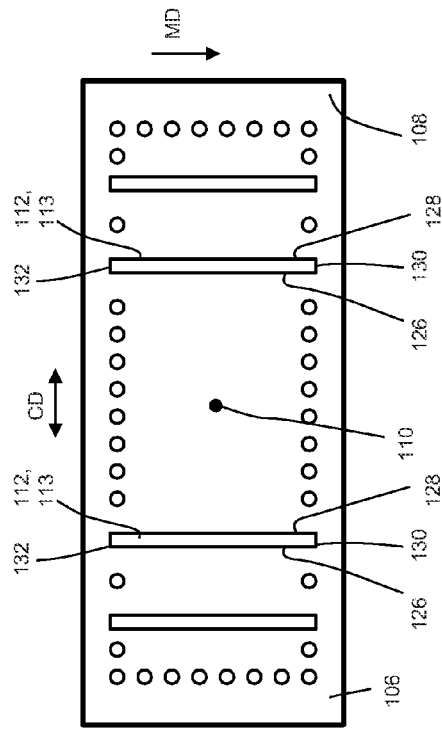
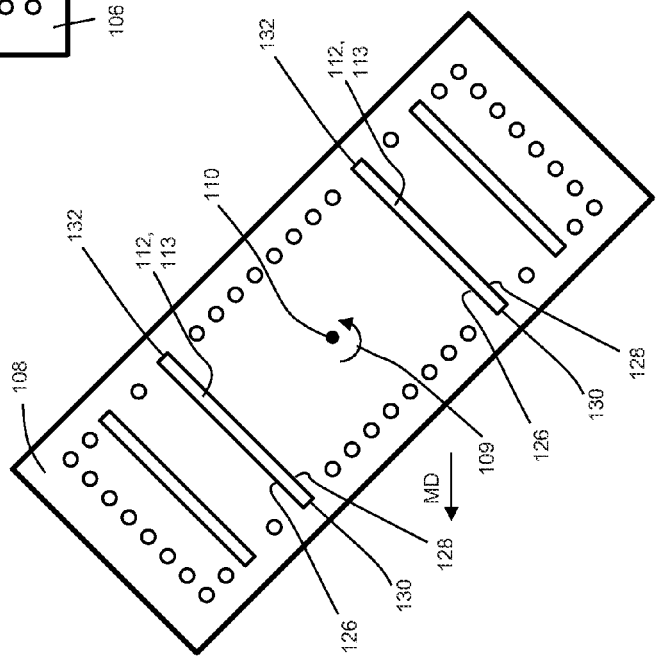

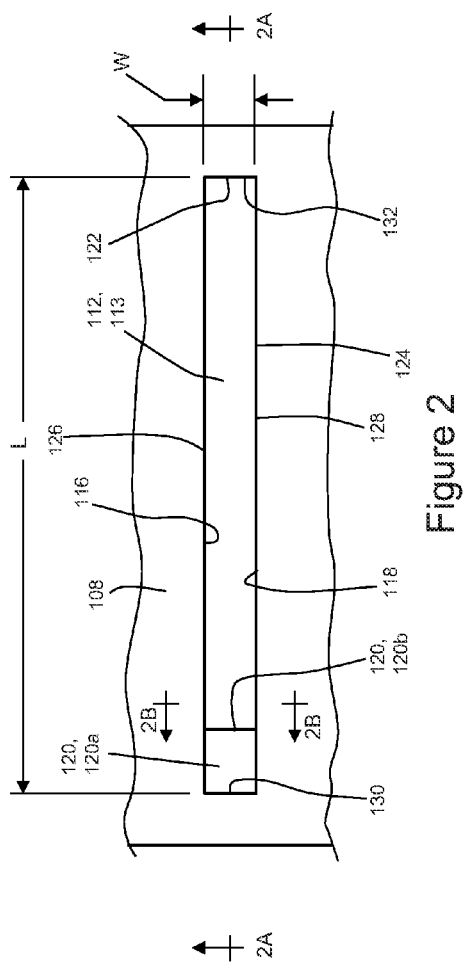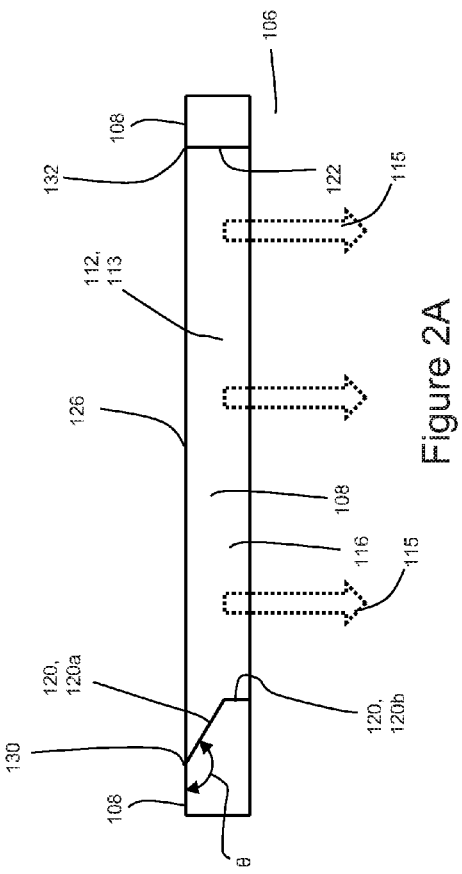

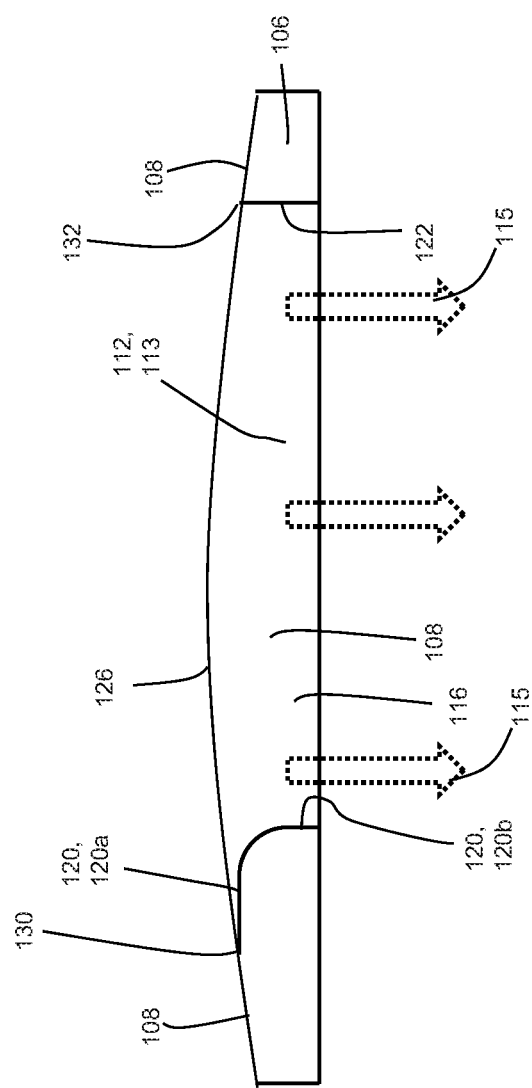

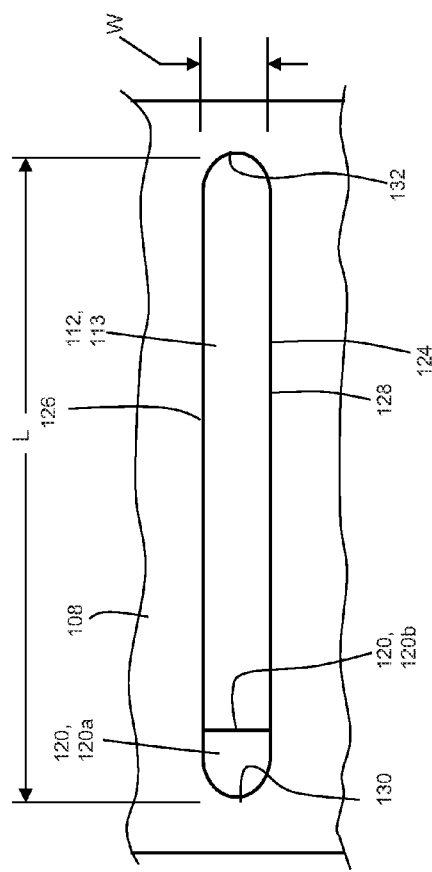
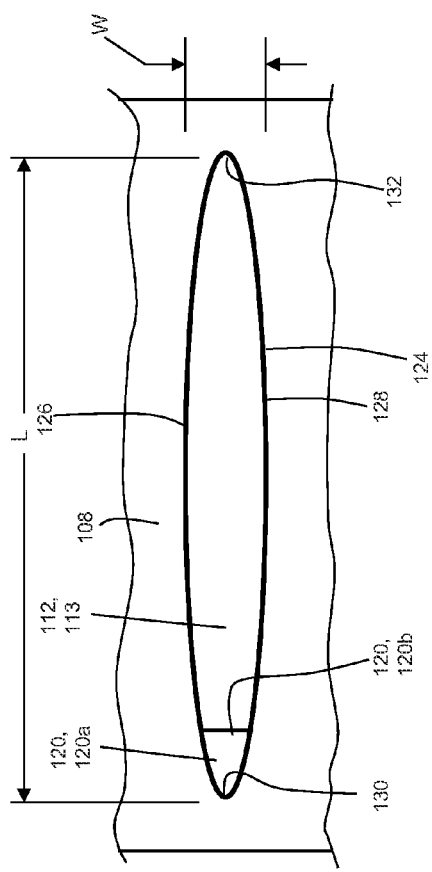
Figure 3
Figure 4

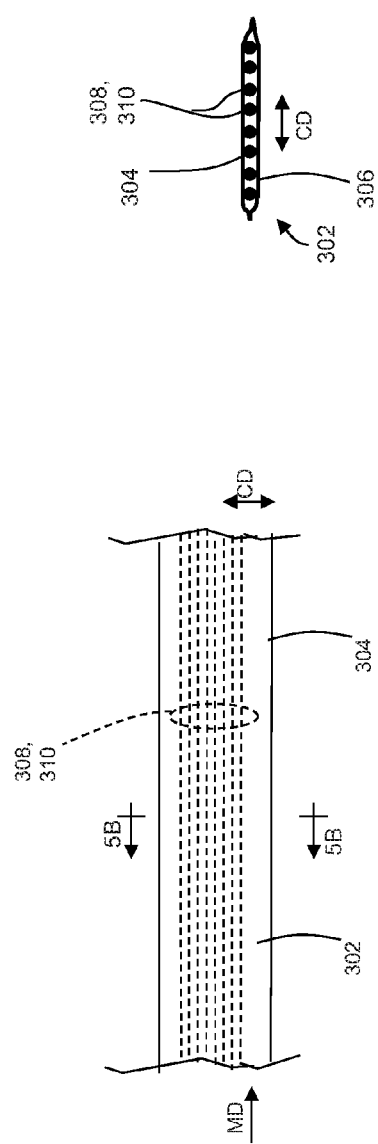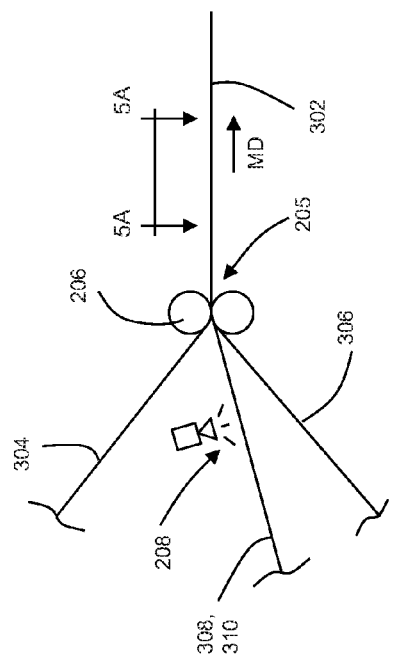
Figure 5A
Figure 5B
Figure 5

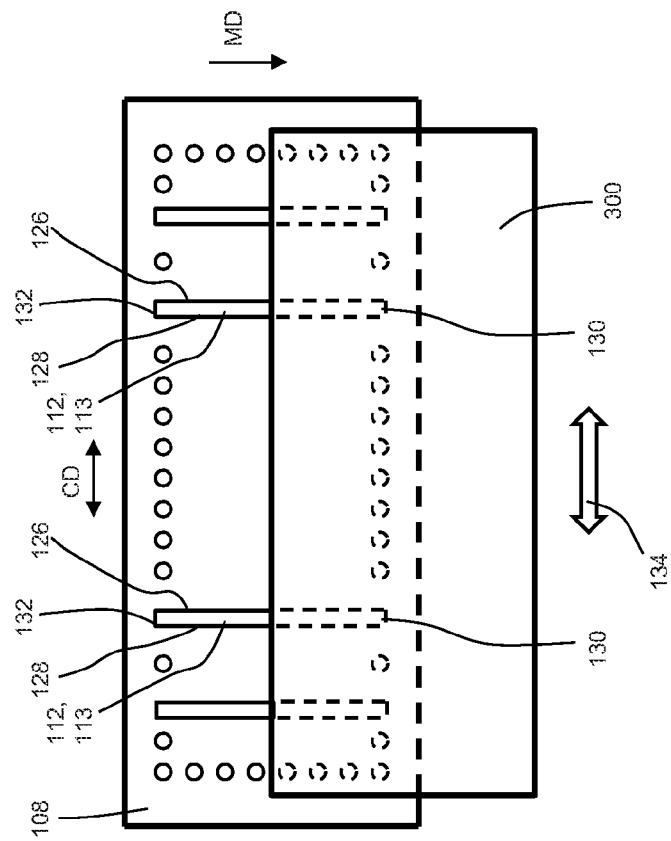
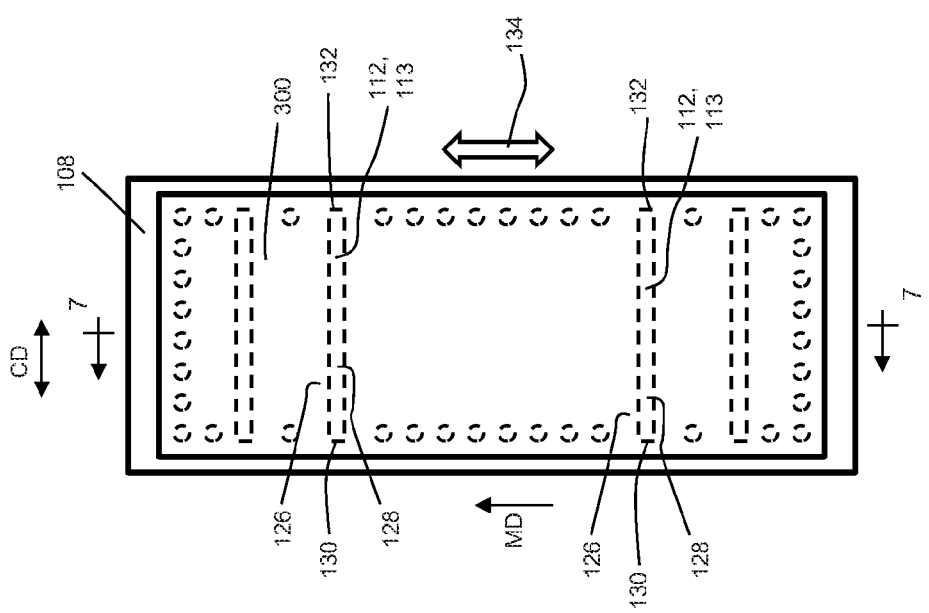
Figure 6B
Figure 6A

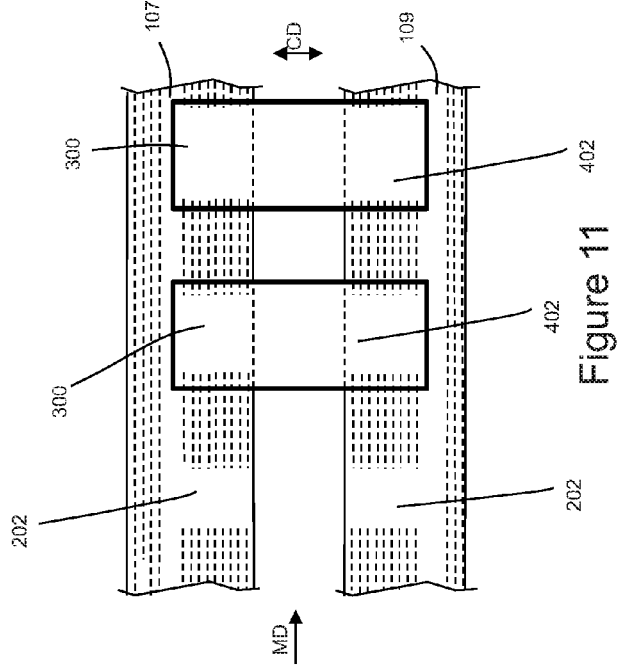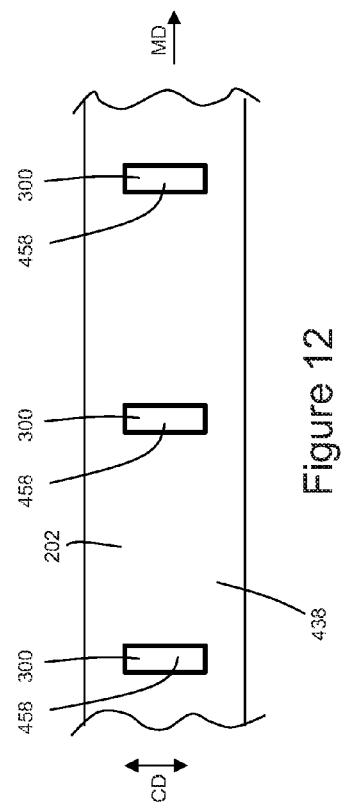

METHOD AND APPARATUS FOR APPLYING ELASTIC PARTS UNDER TENSION TO AN ADVANCING CARRIER

CROSS REFERENCE TO RELATED APPLICATIONS

This application claims the benefit of U.S. Provisional Application No. 62/169,703 filed on Jun. 2, 2015, which is incorporated herein by reference.

FIELD OF THE INVENTION

The present disclosure relates to methods apparatuses for manufacturing absorbent articles, and more particularly, to apparatuses and methods for reorienting and transferring stretched elastic parts during the assembly of absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from an advancing web or webs are combined with other individual components created from other advancing webs. Webs of material and component parts used to manufacture diapers may include: backsheets, topsheets, leg cuffs, waist bands, absorbent core components, front and/or back ears, fastening components, and various types of elastic webs and parts such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

Some absorbent articles have components that include elastic parts, such as for example, elastic laminates. Such elastic laminates may include an elastic material bonded to one or more substrates, such as nonwovens. The elastic material may include an elastic film and/or elastic strands. In some elastic laminates, a plurality of elastic strands are joined to a nonwoven while the plurality of strands are in a stretched condition so that when the elastic strands relax, the nonwoven gathers between the locations where the nonwoven is bonded to the elastic strands forming corrugations. The resulting elastic laminate is stretchable to the extent that the corrugations allow the elastic strands to elongate.

When manufacturing absorbent articles, a continuous elastic laminate may be assembled in a stretched condition. The continuous elastic laminate may be subsequently cut into discrete lengths and subsequently combined with other absorbent article components while maintaining the stretched condition of the discrete elastic laminates. In some assembly configurations, elastic laminates may initially advance in a machine direction through the converting process in a stretched condition wherein the direction of stretch is parallel with the machine direction. The elastic laminates may then be transferred to device, such as a rotating drum, that reorients the elastic laminates by 90 degrees such that the direction of stretch is perpendicular to the machine direction. In a subsequent assembly operation, the reoriented elastic laminate may be combined with another advancing substrate and/or component while maintaining the elastic laminate in a stretched condition.

However, problems can be encountered during the manufacture of absorbent articles with elastic laminates that may be associated with reorientation and/or combining operations while maintaining the elastic laminate in a stretched condition. For example, during a reorientation process, such as mentioned above, elastic laminates may be held in a stretched state on an outer surface of a drum with vacuum pressure. As such, the outer surface of the drum may include apertures in fluid communication with a vacuum source. In some configurations, vacuum pressure may cause portions of the elastic laminate to be partially pushed into the apertures in order to help hold the length elastic laminate on the outer surface a fixed position and prevent undesired contraction. Although having portions of the elastic laminate held in position by the apertures may help to maintain the stretched condition of the elastic laminate, this may cause problems with subsequent assembly operations. For example, portions of the elastic laminate may become stuck or snagged on the aperture edges while attempting to transfer the reoriented elastic laminate from the drum to be combined with another substrate. In some instances, steps may be taken to help mitigate problems associated with stuck or snagged laminates during transfer operations, such as chamfering aperture edges or reducing the vacuum pressure. However, such mitigating steps may adversely affect the ability of the rotating drum to hold the elastic laminate in the desired stretched condition.

Consequently, it would be beneficial to provide a method and apparatus for assembling absorbent articles that helps to maintain an elastic part in a stretched condition as an elastic part is reoriented relative to a machine direction, while at the same time helping to reduce problems associated with sticking and/or snagging of the reoriented elastic part during subsequent transfer and/or assembly operations.

SUMMARY OF THE INVENTION

The present disclosure relates to methods and apparatuses for assembling, advancing, reorienting, and/or transferring stretched elastic parts during the assembly of absorbent articles. As described herein, a continuous elastic substrate may advance in a machine direction in a stretched condition with at least one direction of stretch that extends in the machine direction. A discrete elastic part may be cut from the continuous elastic substrate, while at the same time maintaining the stretched condition of the discrete elastic part. A transfer assembly then reorients the elastic part from a first orientation, wherein the direction of stretch is generally parallel to the machine direction, to a second orientation, wherein the direction of stretch is generally perpendicular to the machine direction. The reoriented elastic part is then transferred to a carrier while maintaining the stretched condition of the elastic part. The transfer assembly may include a carrier surface with apertures in communication with a vacuum source to help hold the elastic part in the stretched state. In turn, the orientation and/or configuration of the apertures relative to the direction of stretch of the elastic part and relative to the machine direction helps to prevent the elastic part from contracting, while at the same time helps to allow the elastic part to slide off the carrier surface and onto the carrier without snagging and/or sticking to aperture perimeter edges.

In one form, a method for transporting a discrete elastic part to a carrier comprises the steps of: providing a frame comprising a first axis of rotation; providing a transfer member rotatably connected with the frame, the transfer member comprising a carrier surface, a first elongate aperture in the carrier surface, and a second elongate aperture in the carrier surface, the first and second elongate apertures each comprising a side edge and a end edge, wherein the side edge is longer than the end edge; rotating the transfer member about the first axis of rotation in a machine direction; rotating the carrier surface about a second axis to a first orientation wherein the side edges of the first and second apertures extend generally perpendicular to the machine direction; positioning the discrete elastic part in a stretched condition on the carrier surface, wherein the carrier surface is in the first orientation; forcing a first portion of the discrete elastic part into the first aperture and a second portion of the discrete elastic part into the second aperture to counteract contraction of the discrete elastic part between the side edge of the first aperture and the side edge of the second aperture; rotating the carrier surface of the transfer member and the discrete elastic part about the second axis of rotation to place the carrier surface in a second orientation wherein the side edges of the first and second apertures extend generally parallel to the machine direction; and sliding the discrete elastic part over the end edges of the first and second apertures in the carrier surface of the transfer member onto a carrier while the carrier surface is in the second orientation.

In another form, a method for transporting a discrete part to a carrier comprises the steps of: providing a transfer member comprising a carrier surface, a first elongate aperture in the carrier surface, and a second elongate aperture in the carrier surface, the first and second elongate apertures each comprising a perimeter defining a maximum width W and a maximum length L, wherein the maximum length L is greater than the maximum width W, and advancing the transfer member in a machine direction; positioning a discrete part in a stretched condition on the carrier surface of the transfer member while the carrier surface is in a first orientation wherein the maximum widths W of the first and second elongate apertures extend generally parallel to the machine direction; forcing a first portion of the discrete part into the first aperture and a second portion of the discrete part into the second aperture to counteract contraction of the discrete part between the first aperture and the second aperture; rotating the discrete part and the carrier surface about a first axis to place the carrier surface in a second orientation wherein the maximum length L of the elongate aperture extends generally parallel to the machine direction; and transferring the discrete part from the carrier surface of the transfer member to a carrier while the carrier surface of the transfer member is in the second orientation.

In yet another form, a transfer assembly for transporting a discrete part in a machine direction from a first position to a carrier at a second position comprises: a frame comprising a first axis; a transfer member movably connected with the frame and adapted to orbit in a machine direction about the first axis, the transfer member comprising: a carrier surface adapted to engage a discrete part, the carrier surface rotatable about a second axis between a first orientation and a second orientation; an elongate aperture in the carrier surface, the elongate aperture comprising a perimeter defining a maximum width W and a maximum length L, wherein the maximum length L is greater than the maximum width W; a vacuum source in communication with the aperture; and wherein the maximum width W of the elongate aperture extends generally parallel to the machine direction when the carrier surface is in the first orientation, and wherein the maximum length L of the elongate aperture extends generally parallel to the machine direction when the carrier surface is in the second orientation.

BRIEF DESCRIPTION OF THE DRAWINGS

FIG. 1A is a view of a carrier surface from FIG. 1 taken along line 1A-1A.

FIG. 1B is a view of a carrier surface from FIG. 1 taken along line 1B-1B.

FIG. 1C is a view of a carrier surface from FIG. 1 taken along line 1C-1C.

FIG. 2 is a detailed view of an elongate aperture in the carrier surface of FIG. 1A.

FIG. 2A is a section view of the elongate aperture of FIG. 2 taken along line 2A-2A.

FIG. 2AA is a section view of an elongate aperture in a curved carrier surface.

FIG. 2B is a section view of the elongate aperture of FIG. 2 taken along line 2B-2B.

FIG. 3 is a detailed view of a second embodiment of an aperture in a carrier surface.

FIG. 4 is a detailed view of a third embodiment of an aperture in a carrier surface.

FIG. 5 is a schematic side view of an apparatus for assembling an elastic substrate.

FIG. 5A is a view of the elastic substrate from FIG. 5 taken along line 5A-5A.

FIG. 5B is a section view of the elastic substrate from FIG. 5A taken along line 5B-5B.

FIG. 6A is a plan view of an elastic part on a carrier surface advancing in a first orientation from FIG. 6 taken along line 6A-6A.

FIG. 6B is a plan view of the elastic part of FIG. 6 partially removed from the carrier surface in a second orientation taken along line 6B-6B.

FIG. 11 is a view of elastic parts in the form of discrete chassis that have been transferred to advancing continuous belt laminates.

FIG. 12 is a view of elastic parts in the form of discrete waistbands that have been transferred to an advancing continuous topsheet or backsheet substrate.

DETAILED DESCRIPTION OF THE INVENTION

Figure 1:
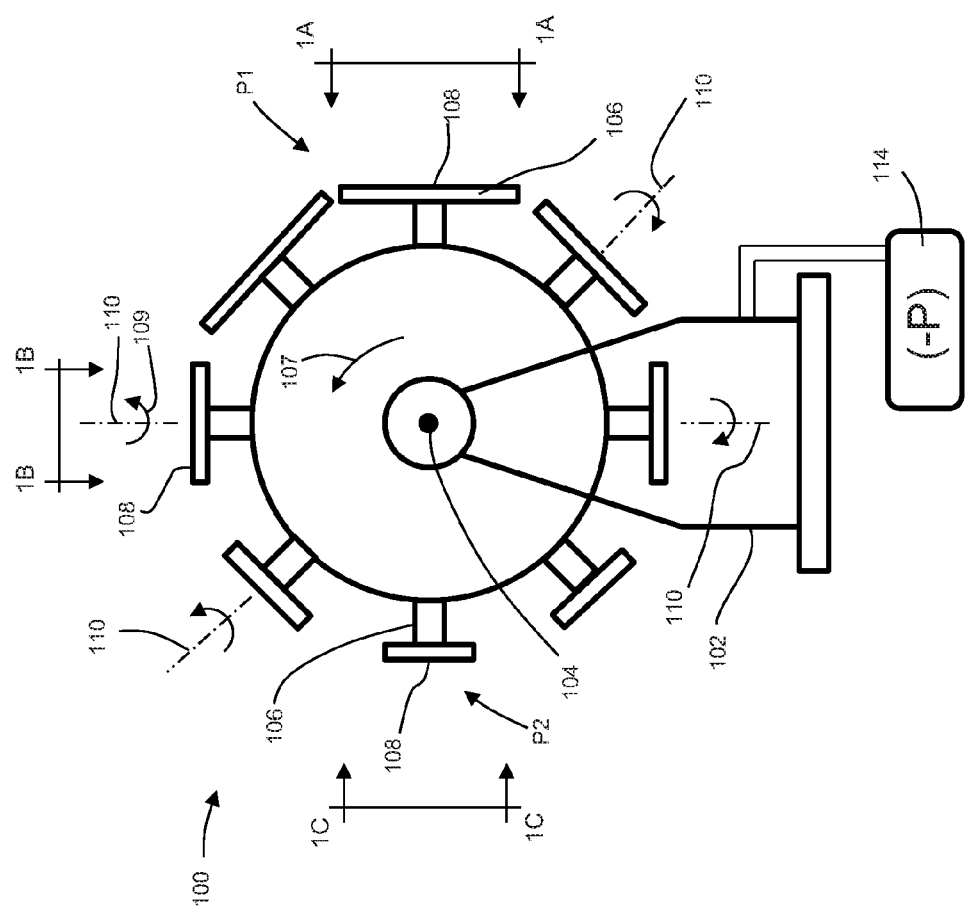
FIG. 1 is a schematic side view of a transfer assembly.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674, 216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 5,246,433; 5,569,234; 6,120,487; 6,120,489; 4,940, 464; 5,092,861; 5,897,545; 5,957,908; and U.S. Patent Publication No. 2003/0233082.

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "substrate" is used herein to describe a material which is primarily two-dimensional (i.e. in an XY plane) and whose thickness (in a Z direction) is relatively small (i.e. $\frac{1}{10}$ or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The present disclosure relates to methods and apparatuses for manufacturing absorbent articles, and in particular, to methods and apparatuses for assembling, advancing, reorienting, and/or transferring stretched elastic parts during the assembly of absorbent articles. With regard to assembly processes described herein, a continuous elastic substrate may advance in a machine direction in a stretched condition with at least one direction of stretch that extends in the machine direction. A discrete elastic part may be cut from the continuous elastic substrate, while at the same time maintaining the stretched condition of the discrete elastic part. The elastic part may then advance to a transfer assembly that reorients the elastic part from a first orientation, wherein the direction of stretch is generally parallel to the machine direction, to a second orientation, wherein the direction of stretch is generally perpendicular to the machine direction. The transfer assembly may then transfer the reoriented elastic part to a carrier while maintaining the stretched condition of the elastic part. The transfer assembly may include a carrier surface with apertures in communication with a vacuum source to help hold the elastic part in the stretched state. As discussed in more detail below, the orientation and/or configuration of the apertures relative to the direction of stretch of the elastic part and relative to the machine direction helps to prevent the elastic part from contracting, while at the same time helps to allow the elastic part to slide off the carrier surface and onto the carrier without snagging and/or sticking to aperture perimeter edges.

FIG. 1 shows an example of a transfer assembly 100 that may be configured to transport a discrete elastic part in a machine direction MD from a first position P1 to a second position P2. For example, as discussed in more detail below with reference to FIG. 6, the transfer assembly 100 may be configured to advance a discrete elastic part 300 from a first position P1 cut from a continuous elastic substrate 302 at a pick-up zone 200 to a second position P2 wherein the elastic part 300 is transferred to a downstream carrier 202 at a drop-off zone 204. With continued reference to FIG. 1, the transfer assembly 100 may include a frame 102 comprising a first axis 104 and one or more transfer members 106 movably and/or rotatably connected with the frame 102 and adapted to rotate as indicated by directional arrow 107 in a machine direction MD about the first axis 104. In turn, each transfer member 106 may include a carrier surface 108 adapted to engage the discrete elastic part 300. As shown in FIGS. 1, 1A, 1B, and 1C, the carrier surface 108 may also be rotatable about a second axis 110 as indicated by directional arrow 109 between a first orientation and a second orientation. Apertures 112 in the carrier surface may be configured to be in communication with a vacuum source 114, and as such, vacuum pressure created by the vacuum source 114 draws air through the apertures 112, as indicated by arrows 115 in FIGS. 2A and 2B. As discussed in more detail below, the vacuum pressure created by the vacuum source 114 in the apertures 112 helps to hold the elastic part 300 on the carrier surface 108.

As shown in FIG. 1A, the apertures 112 in the carrier surface 108 may be configured with different shapes. For example, some of the apertures 112 in the carrier surface 108 may be configured as circular apertures 111 and some may be configured as elongate apertures 113. As shown in FIGS. 2-2B, the elongate aperture 113 may include a first side wall 116 and an opposing second side wall 118 and may include a first end wall 120 and an opposing second end wall 122. It is to be appreciated that the side walls 116, 118 and/or end walls 120, 122 may be configured in various sizes, shapes, and/or orientations. For example, the side walls 116, 118 and/or end walls 120, 122 may be configured to extend away from the carrier surface 108 so as to define straight and/or curved planar surfaces. In addition, the side walls 116, 118 and/or end walls 120, 122 may be oriented at various angles with respect to the carrier surface 108. For example, the side walls 116, 118 and/or end walls 120, 122 may be parallel with each other and/or may be perpendicular to the carrier surface 108. In some examples, the side walls 116, 118 and/or end walls 120, 122 may extend toward each other or away from each other.

With continued reference to FIGS. 2-2B, the apertures 112 may include a perimeter 124 defined by the intersection of the side walls 116, 118 and the end walls 120, 122 with the carrier surface 108. For example, as shown in FIGS. 2-2B, a first side edge 126 of the aperture 113 may be defined by the intersection of the first side wall 116 and the carrier surface 108, and a second side edge 128 may be defined by the intersection of the second side wall 118 and the carrier surface 108. In addition, a first end edge 130 may be defined by the intersection of the first end wall 120 and the carrier surface 108, and a second end edge 132 may be defined by the intersection of the second end wall 122. As such, the perimeter 124 of the elongate aperture 113 may be defined by the first side edge 126, the first side edge 130, the second side edge 128, and the second end edge 132. As shown in FIG. 2, the side edges 116, 118 of the elongate aperture 113 are relatively longer than the end edges 120, 122. As such, the perimeter 124 of the aperture 113 defines a maximum width W and a maximum length L, wherein the maximum length L is greater than the maximum width W. As discussed in more detail below, when carrier surface 108 is in the first orientation such as shown in FIG. 1A, the maximum width W of the elongate aperture 113 extends generally parallel to the machine direction MD. And when in the carrier surface 108 is in the second orientation such as shown in FIG. 1C, the maximum length L of the elongate aperture 113 extends generally parallel to the machine direction MD.

It is also to be appreciated that the perimeter 124 of the elongate apertures 113 discussed herein may be configured with curved and/or straight side edges and/or end edges to define various shapes and sizes. For example, the perimeter 124 of the elongate aperture 113 such as shown in FIG. 2 may include relatively straight side edges 126, 128 and end edges 130, 132 to define a rectangular shape. In another example, the perimeter 124 of the elongate aperture 113 such as shown in FIG. 3 may be defined by straight side edges 126, 128 and curved end edges 130, 132. In yet another example, the perimeter 124 of the elongate aperture 113 such as shown in FIG. 4 may be include curved side edges 126, 128 and curved end edges 130, 132 to define an elliptical shape. It is appreciated that the perimeters 124 of the elongate apertures 113 may define various ratios of maximum lengths L to maximum widths W. For example, in some embodiments, the ratio of the maximum length L to the maximum width W may be from about 6 to about 10. In addition, in some embodiments, the a ratio of a length of the first side edge 126 and/or second side edge 128 to a length of the first end edge 130 and/or second end edge 132 may be equal to or greater than about 6, and may be may be from about 6 to about 10.

It is to be appreciated that the side edges 126, 128 and/or end edges 130, 132 may be configured in various ways. For example, the side edges 126, 128 and/or end edges 130, 132 may be configured as relatively sharp corners at the intersection of the carrier surface 108 and the side walls 116, 118 and/or end walls 120, 122. The side edges 126, 128 and/or end edges 130, 132 may be curved as defined by a relatively smooth transition from the carrier surface 108 to the side walls 116, 118 and/or end walls 120, 122. In some embodiments, the side walls 116, 118 and/or end walls 120, 122 or portions thereof may be tapered relative to the carrier surface 108 to define an edge characterized by a relatively smooth transition from the carrier surface 108 and the side walls 116, 118 and/or end walls 120, 122. For example, as shown in FIGS. 2-2B, the first end wall 120 includes a first portion 120a and a second portion 120b. The intersection between the carrier surface 108 and the first portion 120a defines an angle θ, wherein θ is greater the 90 degrees. In some embodiments such as shown in FIG. 2AA, the carrier surface 108 may be curved such that the side walls 116, 118 and/or end walls 120, 122 or portions thereof may define an edge characterized by a relatively smooth transition from the carrier surface 108 and the side walls 116, 118 and/or end walls 120, 122.

As previously mentioned, the transfer assembly 100 is configured to transports a discrete elastic part 300 in a machine direction MD from a first position P1 to a second position P2. It is to be appreciated that the elastic parts 300 referred to herein may be assembled in various ways. For example, the elastic part 300 may be formed by cutting a discrete length from a continuous elastic substrate 302. In some embodiments, the elastic substrate 302 and/or elastic part 300 may be configured as an elastic material, such as an elastic film, an elastic strand or strands, or combinations thereof. In some embodiments, the elastic substrate 302 and/or elastic part 300 may include an elastic material bonded to one or more substrates. For example, as shown in FIGS. 5-5B, the elastic substrate 302 and/or elastic part 300 may be configured as a laminate that may include a first substrate 304, a second substrate 306, and an elastic material 308 bonded between the first substrate 304 and second substrate 306. Although the elastic material 308 in FIGS. 5-5B is depicted as a plurality of elastics strands 310, it is to be appreciated that the elastic material 308 may be in the form of one or more elastic strands and/or an elastic film, or combinations thereof.

As discussed above, an elastic part 300 may be cut from a continuous elastic substrate 302. As shown in FIG. 5, a continuous or discrete length of elastic material 308 may be advanced and stretched in a machine direction MD and may be joined with adhesive at a combining nip 206 with one or more continuous substrate layers 304, 306 advancing the machine direction MD to form a continuous elastic substrate 302. More particularly, continuous lengths of a first substrate layer 304, a second substrate layer 306, and elastic material 308 in the form of elastic strands 310 are advanced in a machine direction MD and combined at nip rolls 206 to form a continuous length of an elastic substrate 302. Before entering the nip rolls 206, the elastic material 308 is stretched in the machine direction MD. In addition, adhesive 208 may be applied to the elastic material 308 as well as either or both of the continuous lengths of substrate layers 304, 306 before entering nip rolls 206. Although FIG. 5 shows an example process wherein the elastic substrate 302 is formed by combining continuous lengths of first and second substrate layers 304, 306 with elastic material 308, it is to be appreciated the elastic substrate 302 can be formed in various other ways. For example, the first continuous substrate layer 304 and the second continuous substrate layer 306 may be formed by a folding portion of a single continuous substrate onto another portion of the single continuous substrate.

Figure 6:
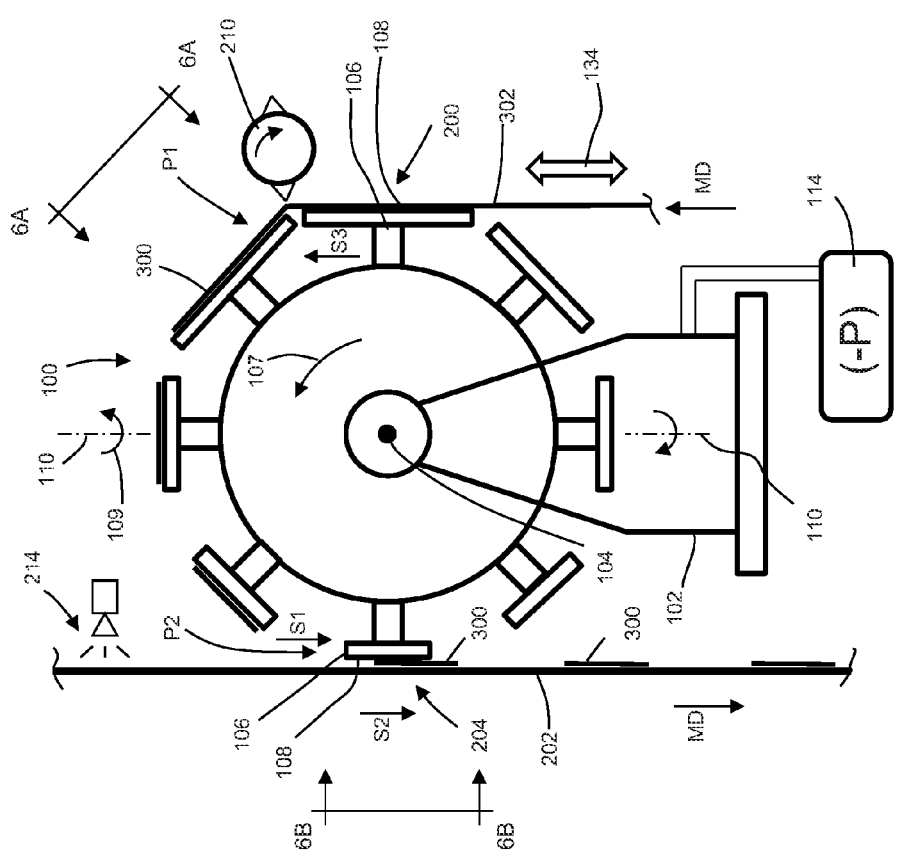
FIG. 6 is schematic side view of a transfer assembly advancing an elastic part cut from an elastic substrate to a carrier at a drop-off zone.

FIG. 6 shows a detailed schematic view of a transfer assembly 100 configured to transport discrete elastic parts 300 in a machine direction MD from a first position P1 to a second position P2. In particular, a continuous elastic substrate 302 advances in a machine direction MD to the transfer assembly 100. The elastic substrate 302 is in a stretched condition wherein the direction of stretch indicated by arrow 134 is parallel or substantially parallel with the machine direction MD. The stretched elastic substrate 302 engages the carrier surface 108 of an advancing transfer member 106 at a pick-up zone 200. As the transfer member 106 is rotated about the first axis 104 as indicated by directional arrow 107 to advance a portion of the stretched elastic substrate 302, a cutter 210 cuts the elastic part 300 from the continuous elastic substrate 302 at the pick-up zone 200. It is to be appreciated that the cutter 210 may be configured in various ways, such as for example, a knife or a laser. In some embodiments, the transfer assembly 100 may include anvils positioned between adjacent transfer members 106 that engage a knife. In other embodiments, the transfer assembly 100 may include knife edges between adjacent transfer members that engage and an adjacent anvil roll.

Figure 7:
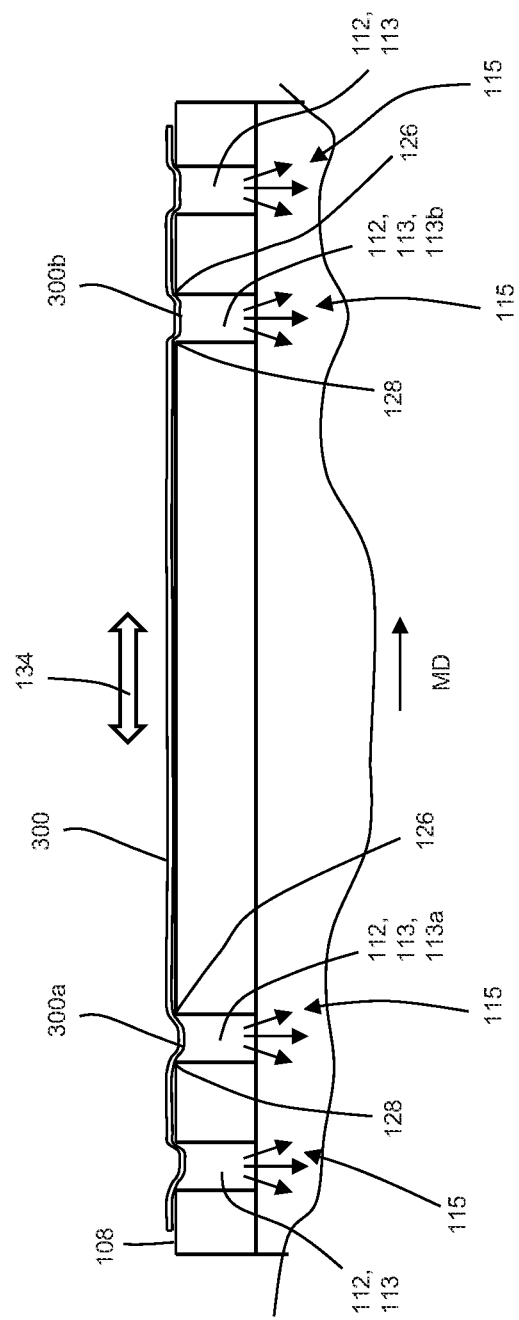
FIG. 7 is section view of the elastic part and carrier surface of FIG. 6A taken along line 7-7.

As shown in FIGS. 6, 6A, and 7, the discrete elastics part 300 is positioned on the carrier surface 108 in a stretched condition while the carrier surface 108 and the elastic part are in first orientations. In particular, in the first orientation, the direction of stretch 134 of the elastic part 300 is parallel or substantially parallel with the machine direction MD. And as discussed above with reference to FIG. 1A, when carrier surface 108 is in the first orientation, the relatively long side edges 126, 128 of the apertures 113 may be parallel or substantially parallel with the machine direction MD, and the relatively short end edges 130, 132 of the apertures 113 may be perpendicular or substantially perpendicular to the machine direction MD. As such, in the first orientation, the maximum width W of the elongate aperture 113 extends parallel to or substantially parallel with the machine direction MD.

As shown in FIGS. 6A and 7, the elastic part 300 in the first orientation is positioned on the carrier surface 108 such that the relatively long side edges 126, 128 of the apertures 113 are perpendicular or substantially perpendicular to the direction of stretch 134, and the relatively short end edges 130, 132 of the apertures 113 are parallel or substantially parallel with the direction of stretch 134. As shown in FIG. 7, forces created by vacuum pressure 115 acting on the elastic part 300 forces a first portion 300a of the discrete elastic part 300 into a first aperture 113a and a second portion 300b of the discrete elastic part 300 into the second aperture 113b. As previously mentioned, the elastic part 300 having a direction of stretch 134 is maintained in a stretched condition on the carrier surface 108. As such, the elastic part 300 tends to contract in a direction opposite the direction of stretch 134. The portions 300a, 300b of the elastic part 300 forced into the apertures 113a, 113b overlap the first side edge 126 of the first aperture 113a and the second side edge 128 of the second aperture 113b. The overlapping of the elastic part 300 over the side edges 126, 128 of the apertures 113a, 113b helps prevent the portions 300a, 300b of the elastic part 300 from sliding toward each other along the carrier surface 108. Thus, forcing portions 300a, 300b of the discrete elastic part 300 into the apertures 113a, 113b helps to counteract contraction of the discrete elastic part 300 between the first side edge 126 of the first aperture 113a and the second side 128 edge of the second aperture 113b.

Referring now to FIGS. 6 and 6B, the transfer member 106 is rotated about the first axis 104 from the first position P1 to the second position P2. As such, the carrier surface 108 and the elastic part 300 positioned on the carrier surface 108 orbit about the first axis 104 from the first position P1 to the second position P2. While orbiting from the first position P1 to the second position P2, the carrier surface 108 and the discrete elastic part 300 are rotated about the second axis of rotation 110 to place the carrier surface 108 and the elastic part 300 in a second orientation. In particular, in the second orientation, the direction of stretch 134 of the elastic part 300 is perpendicular or substantially perpendicular to the machine direction MD. And as discussed above with reference to FIG. 1C, when carrier surface 108 is in the second orientation, the relatively long side edges 126, 128 of the apertures 113 may be perpendicular or substantially perpendicular to the machine direction MD, and the relatively short end edges 130, 132 of the apertures 113 may be parallel or substantially parallel to the machine direction MD. As such, in the second orientation, the maximum width W of the elongate aperture 113 extends perpendicular to or substantially perpendicular to the machine direction MD.

With continued reference to FIGS. 6 and 6B, the carrier surface 108 and the discrete elastic part 300 are advanced to the second position P2 in the second orientation, and the elastic part 300 is transferred to an advancing downstream carrier 202 at the drop-off zone 204. In some configurations, the elastic part 300 may slide along the carrier surface 108 and onto downstream carrier 202 at the drop-off zone 204 while the carrier surface 108 is in the second orientation. As such, portions 300a, 300b of the elastic part may slide over the first end edges 130 of the first and second apertures 113a, 113b while being transferred to the downstream carrier 202. Thus, the orientation of the relatively short end edges 130 of the apertures 113a, 113b being generally parallel to the direction of stretch 134 helps to allow the elastic part 300 to slide off the carrier surface 108 without snagging and/or sticking to the aperture perimeter edges.

It is to be appreciated that the downstream carrier 202 may be configured in various ways. For example, in some embodiments, the downstream carrier 202 may be in the form of a conveyor belt or a rotating conveyance device, such as a drum. In some embodiments, the downstream carrier 202 may be in the form of a substrate that may be incorporated into an absorbent article. Examples of such substrates are described in more detail below with reference to FIGS. 9A-10, such as for example, a continuous or discrete topsheet or backsheet substrate. In addition, as shown in FIG. 6, adhesive 214 may be applied to the downstream carrier 202 to help secure the transferred elastic parts 300 thereto. In some embodiments, adhesive may be applied to the elastic part 300 and/or the continuous elastic substrate 302 to help adhere the elastic parts 300 to the downstream carrier 202.

As previously mentioned, the carrier surface 108 is configured such that the orientation of the relatively long side edges 126, 128 of the apertures 113a, 113b and/or the maximum length of the apertures 113a, 113b, being generally perpendicular to the direction of stretch 134 helps to prevent the elastic part 300 from contracting while advancing from the first position P1 to the second position P2 and while being reoriented from the first orientation to the second orientation. At the same time, the orientation of the relatively short end edges 130 of the apertures 113a, 113b and/or the maximum width W of the apertures 113a, 113b being generally parallel to the direction of stretch 134 helps to allow the elastic part 300 to slide off the carrier surface 108 and onto the downstream carrier 202 without snagging and/or sticking to the aperture perimeter edges. As mentioned above, the end edges 130, 132 may be configured to also help the elastic part 300 slide off the carrier surface 108 and onto the downstream carrier 202 without snagging and/or sticking to the aperture perimeter edges. For example, the end edges 130, 132 may be curved as defined by a relatively smooth transition from the carrier surface 108 to end walls 120, 122. In some embodiments, such as discussed above with reference to FIGS. 2-2B, the end walls 120, 122 or portions thereof may be tapered relative to the carrier surface 108 to define an edge characterized by a relatively smooth transition from the carrier surface 108 and the end walls 120, 122. For example, as depicted, the first end wall 120 may include the tapered first portion 120a.

Figure 8:
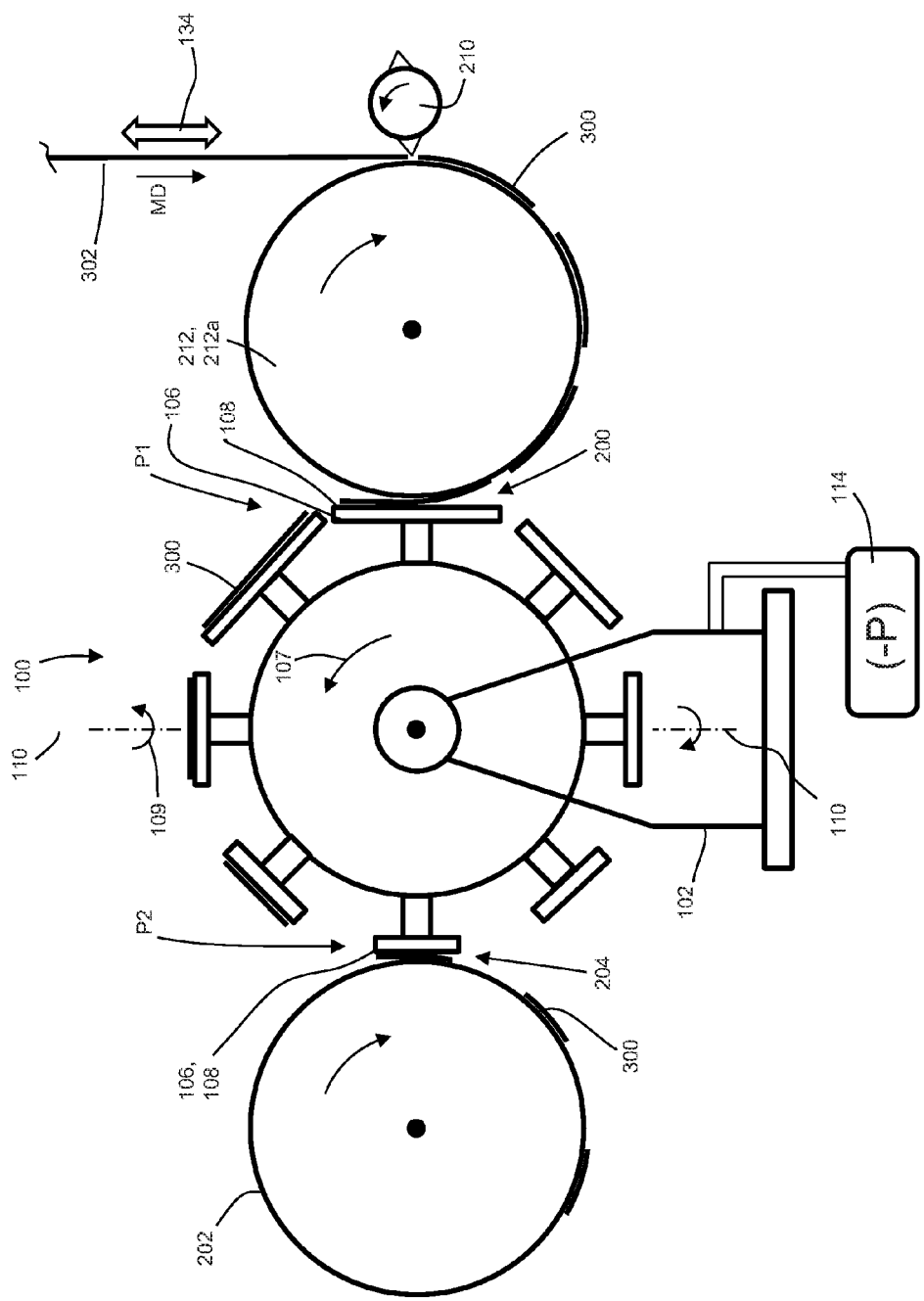
FIG. 8 is schematic side view of a transfer assembly transferring elastic parts from a pick-up zone to a drop off zone.

It is to be appreciated that apparatuses and processes described above may be configured and/or arranged in various ways to transport an elastic part 300 from a first position P1 to a second position P2, reorienting the elastic part 300 from a first orientation to a second orientation, and transferring the elastic part 300 to a downstream carrier 202 while in the second orientation. For example, FIG. 8 shows a process arrangement wherein a continuous elastic substrate 302 advances in a machine direction MD to an upstream carrier 212. Although the upstream carrier 212 is depicted as rotating drum 212a, it is to be appreciated that the upstream carrier 212 may be configured in various ways. For example, in some embodiments, the upstream carrier 202 may be in the form of a conveyor belt or in the form of a substrate that may be incorporated into an absorbent article. The elastic substrate 302 is in a stretched condition wherein the direction of stretch indicated by arrow 134 is parallel or substantially parallel with the machine direction MD. The stretched elastic substrate 302 engages the upstream carrier 212 and a cutter 210 cuts the elastic part 300 from the continuous elastic substrate 302. The upstream carrier 212 advances the elastic part 300 to the transfer assembly 100, wherein the elastic part 300 is transferred from the upstream carrier 212 to the carrier surface 108 in a stretched state at the pick-up zone 200. As discussed above, the transfer member 106 is rotated about the first axis 104 from the first position P1 to the second position P2. In addition, the carrier surface 108 and the elastic part 300 positioned on the carrier surface 108 orbit about the first axis 104 from the first position P1 to the second position P2. While orbiting from the first position P1 to the second position P2, the carrier surface 108 and the discrete elastic part 300 are rotated about the second axis of rotation 110 to place the carrier surface 108 and the elastic part 300 in a second orientation. And the elastic part 300 is then transferred to a downstream carrier 202 at the drop-off zone 204.

It is to be appreciated that the carrier surfaces 108 disclosed herein may operate with transfer assemblies configured in various ways, such as disclosed for example in U.S. Pat. Nos. 5,025,910; 5,224,405; 5,556,504; 6,319,347; 6,450,321; 6,604,623; 6,116,317; 6,722,494; 7,341,087; 7,650,984; 7,770,712; and 8,720,666, all of which are incorporated by reference herein. For example, the carrier surface 108 may advance at various speeds through the drop-off zone 204 relative to the speed of the downstream carrier 202. For example, the carrier surface 108 may advance at a first speed S1 through the drop-off zone 204 and the downstream carrier 202 may advance at a second speed S2 through the drop-off zone 204. In some embodiments, the first speed S1 may be equal to or substantially equal to the second speed S2. In some embodiments, the first speed S1 may be greater than the second speed S2. In some embodiments, the transfer assembly 100 may be configured such that the carrier surface 108 advances through the pick-up zone 200 at a third speed S3 and advances through the drop-off zone at the first speed S1, wherein the first speed S1 and the third speed S3 are equal or substantially equal. In some embodiments, the first speed S1 may be less than or greater than the third speed S3. As such, in some embodiments, the transfer assembly 100 may be configured to rotate the transfer member 106 about the first axis 104 at a constant or variable angular velocity. In some embodiments, the carrier surface 108 may orbit the first axis 104 at a constant or variable angular velocity and/or at a constant or variable speed. In some embodiments, the carrier surface 108 may orbit the first axis 104 at a constant or variable distance from the first axis 104. It is also to be appreciated that the carrier surface 108 herein may be arranged with various quantities of apertures having various shapes and sizes.

As previously mentioned, the processes and apparatuses discussed herein may be used in the manufacture of different types of absorbent articles. More particularly, the elastic parts discussed herein may be used as to construct various different components used in the manufacture of different types of absorbent articles. To help provide additional context to the subsequent discussion of the process and apparatus embodiments, the following provides a general description of absorbent articles in the form of diapers that include various components that may be constructed from the elastic parts using the apparatuses and methods disclosed herein.

Figure 9A:
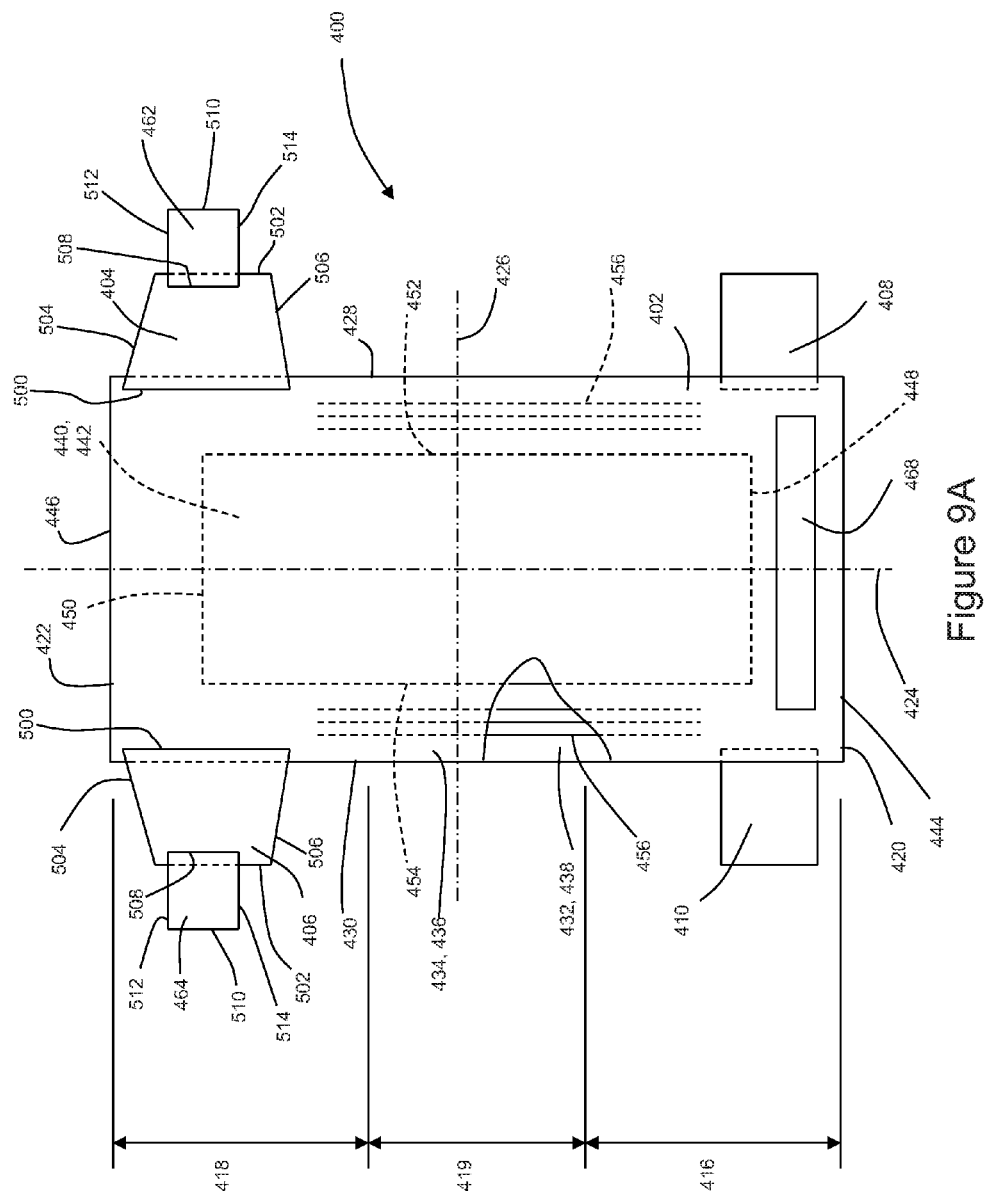
FIG. 9A is a partially cut away plan view of a taped diaper with the portion of the diaper that faces away from a wearer oriented towards the viewer.
Figure 9B:
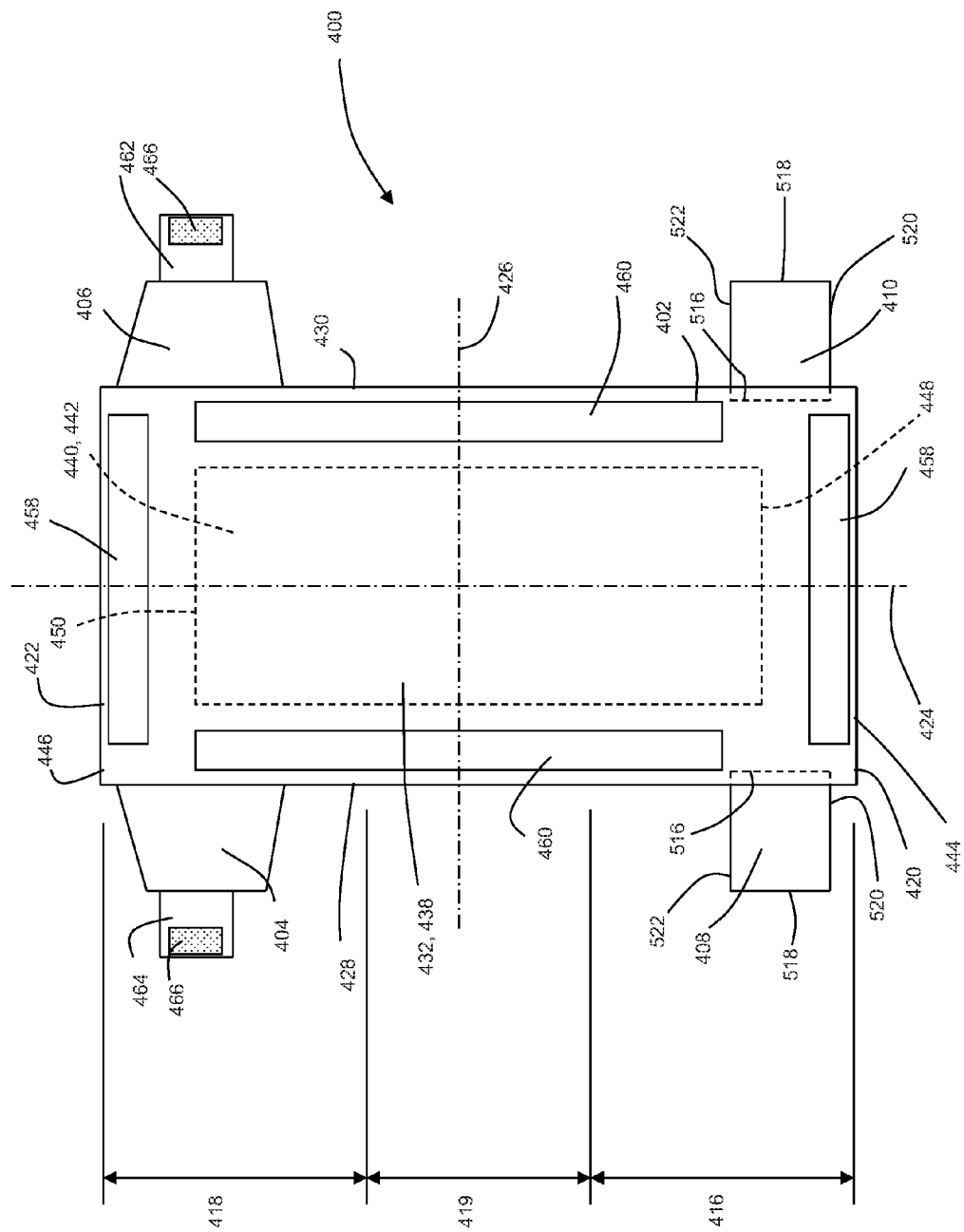
FIG. 9B is a plan view of the taped diaper of FIG. 9A with the portion of the diaper that faces toward a wearer oriented towards the viewer.

FIGS. 9A and 9B show an example of an absorbent article 100 that may be assembled in accordance with the methods disclosed herein. In particular, FIG. 9A shows one example of a plan view of an absorbent article configured as a taped diaper 400, with the portion of the diaper that faces away from a wearer oriented towards the viewer. And FIG. 9B shows a plan view of the diaper 400 with the portion of the diaper that faces toward a wearer oriented towards the viewer. The taped diaper 400 shown in FIGS. 9A and 9B includes a chassis 402, first and second rear side panels 404 and 406; and first and second front side panels 408 and 410.

As shown in FIGS. 9A and 9B, the diaper 400 and the chassis 402 each include a first waist region 416, a second waist region 418, and a crotch region 419 disposed intermediate the first and second waist regions. The first waist region 416 may be configured as a front waist region, and the second waist region 418 may be configured as back waist region. In some embodiments, the length of each of the front waist region, back waist region, and crotch region may be ⅓ of the length of the absorbent article 400. The absorbent article may also include a laterally extending front waist edge 420 in the front waist region 416 and a longitudinally opposing and laterally extending back waist edge 422 in the back waist region 418. To provide a frame of reference for the present discussion, the diaper 400 in FIGS. 9A and 9B are shown with a longitudinal axis 424 and a lateral axis 426. The longitudinal axis 424 may extend through a midpoint of the front waist edge 420 and through a midpoint of the back waist edge 422. And the lateral axis 426 may extend through a midpoint of a first longitudinal or right side edge 428 and through a midpoint of a second longitudinal or left side edge 430.

As shown in FIGS. 9A and 9B, the diaper 400 includes an inner, body facing surface 432, and an outer, garment facing surface 434. And the chassis 402 may include a backsheet 436 and a topsheet 438. The chassis 402 may also include an absorbent assembly 440, including an absorbent core 442, disposed between a portion of the topsheet 438 and the backsheet 436. As discussed in more detail below, the diaper 400 may also include other features, such as leg elastics and/or leg cuffs, an elastic waist region, and/or flaps, e.g., side panels and/or ears, to enhance the fits around the legs and waist of the wearer, to enhance the fit around the legs of the wearer.

As shown in FIGS. 9A and 9B, the periphery of the chassis 402 may be defined by the first longitudinal side edge 428, a second longitudinal side edge 430, a first laterally extending end edge 444 disposed in the first waist region 416, and a second laterally extending end edge 446 disposed in the second waist region 418. Both side edges 428 and 430 extend longitudinally between the first end edge 444 and the second end edge 446. As shown in FIG. 9A, the laterally extending end edges 444 and 446 may form a portion of the laterally extending front waist edge 420 in the front waist region 416 and a portion of the longitudinally opposing and laterally extending back waist edge 422 in the back waist region 418. When the diaper 400 is worn on the lower torso of a wearer, the front waist edge 420 and the back waist edge 422 may encircle a portion of the waist of the wearer. At the same time, the side edges 428 and 430 may encircle at least a portion of the legs of the wearer. And the crotch region 419 may be generally positioned between the legs of the wearer with the absorbent core 442 extending from the front waist region 416 through the crotch region 419 to the back waist region 418.

It is to also be appreciated that a portion or the whole of the diaper 400 may also be elastic and made laterally extensible. The additional extensibility may help allow the diaper 400 to conform to the body of a wearer during movement by the wearer. The additional extensibility may also help, for example, the user of the diaper 400, including a chassis 402 having a particular size before extension, to extend the front waist region 416, the back waist region 418, or both waist regions of the diaper 400 and/or chassis 402 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper 400 may include a backsheet 436. The backsheet 436 may also define the outer surface 434 of the chassis 402. The backsheet 436 may be impervious to fluids (e.g., menses, urine, and/or runny feces) and may be manufactured in part from a thin plastic film, although other flexible liquid impervious materials may also be used. The backsheet 436 may prevent the exudates absorbed and contained in the absorbent core from wetting articles which contact the diaper 400, such as bedsheets, pajamas and undergarments. The backsheet 436 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 436 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 436 may also be embossed and/or matte-finished to provide a more clothlike appearance. Further, the backsheet 436 may permit vapors to escape from the absorbent core (i.e., the backsheet is breathable) while still preventing exudates from passing through the backsheet 436. The size of the backsheet 436 may be dictated by the size of the absorbent core 442 and/or particular configuration or size of the diaper 400.

Also described above, the diaper 400 may include a topsheet 438. The topsheet 438 may also define all or part of the inner surface 432 of the chassis 402. The topsheet 438 may be compliant, soft feeling, and non-irritating to the wearer's skin. It may be elastically stretchable in one or two directions. Further, the topsheet 438 may be liquid pervious, permitting liquids (e.g., menses, urine, and/or runny feces) to penetrate through its thickness. A topsheet 438 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 438 includes fibers, the fibers may be spunbond, carded, wet-laid, meltblown, hydroentangled, or otherwise processed as is known in the art.

Topsheets 438 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper 400 may also include an absorbent assembly 440 that is joined to the chassis 402. As shown in FIGS. 9A and 9B, the absorbent assembly 440 may have a laterally extending front edge 448 in the front waist region 416 and may have a longitudinally opposing and laterally extending back edge 450 in the back waist region 418. The absorbent assembly may have a longitudinally extending right side edge 452 and may have a laterally opposing and longitudinally extending left side edge 454, both absorbent assembly side edges 452 and 454 may extend longitudinally between the front edge 448 and the back edge 450. The absorbent assembly 440 may additionally include one or more absorbent cores 442 or absorbent core layers. The absorbent core 442 may be at least partially disposed between the topsheet 438 and the backsheet 436 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 400 may also include elasticized leg cuffs 456 and an elasticized waistband 458. It is to be appreciated that the leg cuffs 456 can be and are sometimes also referred to as leg bands, side flaps, barrier cuffs, elastic cuffs or gasketing cuffs. The elasticized leg cuffs 456 may be configured in various ways to help reduce the leakage of body exudates in the leg regions. Example leg cuffs 456 may include those described in U.S. Pat. Nos. 3,860,003; 4,909,803; 4,695,278; 4,795,454; 4,704,115; and U.S. Patent Publication No. 2009/0312730 A1.

The elasticized waistband 458 may provide improved fit and containment and may be a portion or zone of the diaper 400 that may elastically expand and contract to dynamically fit a wearer's waist. The elasticized waistband 458 may extend longitudinally inwardly from the waist edges 420, 422 of the diaper toward the lateral edges 448, 450 of the absorbent core 442. The diaper 400 may also include more than one elasticized waistband 458, for example, having one waistband 458 positioned in the back waist region 418 and one waistband 458 positioned in the front wait region 416, although other embodiments may be constructed with a single elasticized waistband 458. The elasticized waistband 458 may be constructed in a number of different configurations including those described in U.S. Pat. Nos. 4,515,595 and 5,151,092. In some embodiments, the elasticized waistbands 458 may include materials that have been "prestrained" or "mechanically prestrained" (subjected to some degree of localized pattern mechanical stretching to permanently elongate the material). The materials may be prestrained using deep embossing techniques as are known in the art. In some embodiments, the materials may be prestrained by directing the material through an incremental mechanical stretching system as described in U.S. Pat. No. 5,330,458. The materials are then allowed to return to their substantially untensioned condition, thus forming a zero strain stretch material that is extensible, at least up to the point of initial stretching. Examples of zero strain materials are disclosed in U.S. Pat. Nos. 2,075,189; 3,025,199; 4,107,364; 4,209,563; 4,834,741; and 5,151,092.

As shown in FIG. 9B, the chassis 402 may include longitudinally extending and laterally opposing side flaps 460 that are disposed on the interior surface 432 of the chassis 402 that faces inwardly toward the wearer and contacts the wearer. Each side flap may have a proximal edge. The side flaps may also overlap the absorbent assembly 440, wherein the proximal edges extend laterally inward of the respective side edges of the absorbent assembly 452 and 454. In some configurations, the side flaps may not overlap the absorbent assembly. It is to be appreciated that the side flaps may be formed in various ways, such as for example, by folding portions of the chassis 402 laterally inward, i.e., toward the longitudinal axis 424, to form both the respective side flaps and the side edges 428 and 430 of the chassis 402. In another example, the side flaps may be formed by attaching an additional layer or layers to the chassis at or adjacent to each of the respective side edges and of the chassis. Each of the side flaps may be joined to the interior surface 432 of the chassis and/or the absorbent assembly in side flap attachment zones in the front waist region 416 and in side flap attachment zones in the back waist region 418. The side flaps may extend to the same longitudinal extent as the absorbent article or alternatively the side flaps may have a longitudinal extent that is less than the absorbent article.

Taped diapers may be manufactured and provided to consumers in a configuration wherein the front waist region and the back waist region are not fastened, pre-fastened, or connected to each other as packaged, prior to being applied to the wearer. For example, the taped diaper 400 may be folded about a lateral centerline with the interior surface 432 of the first waist region 416 in surface to surface contact with the interior surface 432 of the second waist region 418 without fastening or joining the waist regions together. The rear side panels 404 and 406 and/or the front side panels 408 and 410 may also be folded laterally inward toward the inner surfaces 432 of the waist regions 416 and 418.

The diaper 400 may also include various configurations of fastening elements to enable fastening of the front waist region 416 and the back waist region 418 together to form a closed waist circumference and leg openings once the diaper is positioned on a wearer. For example, as shown in FIGS. 9A and 9B, the diaper 400 may include first and second fastening members 462, 464, also referred to as tabs, connected with the first and second rear side panels 404, 406, respectively. The diaper may also include first and second front side panels 408, 410, that may or may not include fastening members.

Referring back to FIGS. 9A and 9B, each rear side panel 404, 406 may include an inner longitudinal side edge 500, an outer longitudinal side edge 502, an outer lateral side edge 504, and an inner lateral side edge 506. In addition, each fastening member 462, 464 may also include an inner longitudinal side edge 508, an outer longitudinal side edge 510, an outer lateral side edge 512, and an inner lateral side edge 514. As shown in FIG. 9A, proximal regions adjacent the inner longitudinal side edges 500 of the rear side panels 404, 406 may be connected with the backsheet 436 of the chassis 402. In addition, proximal regions adjacent the inner longitudinal side edges 508 of the fastening members 462, 464 may be connected with distal regions of the rear side panels 404, 406 adjacent the outer longitudinal side edges 502. As shown in FIG. 9B, each front side panel 408, 410 may include an inner longitudinal side edge 516, an outer longitudinal side edge 518, an outer lateral side edge 520, and an inner lateral side edge 522. As such, proximal regions adjacent the inner longitudinal side edges 516 of the front side panels 408, 410 may be connected with the topsheet 438 of the chassis 402. It is also to be appreciated that the rear side panels 404, 406 may be defined as discrete pieces and may also be defined by opposing end portions of a continuous belt. Similarly, the front side panels 408, 410 may be defined as discrete pieces and may also be defined by opposing end portions of a continuous belt. Examples of such belted configurations are disclosed in U.S. Patent Publication No. 2013/0306226 A1.

With continued reference to FIGS. 9A and 9B, each side panel 404, 406 and/or fastening member 462 and 464 may form a portion of or may be permanently bonded, adhered or otherwise joined directly or indirectly to the chassis 402 laterally inward from the side edge 428 and 430, in one of the front waist region 416 or the back waist region 418. Alternatively, the fastening members 462, 464 may form a portion of or may be permanently bonded, adhered or otherwise joined directly or indirectly to the first and second rear panels 404, 406 at or adjacent the distal edge of the panel and/or the first and second front side panels 408 and 410 at or adjacent the distal edge of the side panel. It is to be appreciated that the fastening members and/or side panels may be assembled in various ways, such as disclosed for example, in U.S. Pat. No. 7,371,302. The fastening members 462, 464 and/or side panels 404, 406, 408, 410 may also be permanently bonded or joined at or adjacent the side edges 428 and 430 of the chassis 402 in various ways, such as for example, by adhesive bonds, sonic bonds, pressure bonds, thermal bonds or combinations thereof, such as disclosed for example, U.S. Pat. No. 5,702,551.

It is to be appreciated that the rear side panels 404, 406 and/or the front side panels 408, 410 may comprise the same materials and/or may have the same structure. In some embodiments, the rear side panels 404, 406 and the front side panels 408, 410 may comprise different materials and/or may have different structures. It should also be appreciated that the rear side panels 404, 406 and the front side panels 408, 410 may be constructed from various materials. For example, the front and/or rear side panels may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the front and/or rear side panels include a nonwoven web of synthetic fibers, and may include a stretchable nonwoven. In other embodiments, the front and/or side panels include an inner hydrophobic, non-stretchable nonwoven material and an outer hydrophobic, non-stretchable nonwoven material.

The rear side panels 404, 406 and/or the front side panels 408, 410 may also be elastic and may each include elastic material interposed between an outer substrate layer and the inner substrate layer. The elastic material may include one or more elastic elements such as strands, ribbons, films, or panels. In some configurations, the rear side panels 404, 406 and/or the front side panels 408, 410 may also define curved contours.

Referring now to FIG. 9B, the first fastening member 462 and/or the second fastening member 464 may include various types of releasably engageable fasteners. The first and second fastening members 462 and/or 464 may also include various types of refastenable fastening structures. For example, the first and second fastening members 462 and 464 may include mechanical fasteners, 466, in the form of hook and loop fasteners, hook and hook fasteners, macrofasteners, buttons, snaps, tab and slot fasteners, tape fasteners, adhesive fasteners, cohesive fasteners, magnetic fasteners, hermaphrodidic fasteners, and the like. Some examples of fastening systems and/or fastening members 462, 464 are discussed in U.S. Pat. Nos. 3,848,594; 4,662,875; 4,846, 815; 4,894,060; 4,946,527; 5,151,092; 5,221,274; 6,251, 097; 6,669,618; 6,432,098; and U.S. Patent Publication Nos. 2007/c and 2007/0093769.

As previously mentioned, the fastening members 462 and 464 may be constructed from various materials and may be constructed as a laminate structure. The fastening members 462 and 464 may also be adapted to releasably and/or refastenably engage or connect with another portion of the diaper 400. For example, as shown in FIG. 9A, the diaper 400 may include a connection zone 468, sometimes referred to as a landing zone, in the first waist region 416. As such, when the taped diaper 400 is placed on a wearer, the fastening members 462 and 464 may be pulled around the waist of the wearer and connected with the connection zone 468 in the first waist region 416 to form a closed waist circumference and a pair of laterally opposing leg openings. It is to be appreciated that the connection zone may be constructed from a separate substrate that is connected with the chassis 402 of the taped diaper. In some embodiments, the connection zone may be integrally formed as part of the backsheet 436 of the diaper 400 or may be formed as part of the first and second front panels 408, 410, such as described in U.S. Pat. Nos. 5,735,840 and 5,928,212.

As previously mentioned, diapers 400 may also be provided in the form of a pant-type diaper. For example, the diaper 400 discussed above with reference to FIGS. 9A and 9B may configured as a diaper pant with pre-formed by permanently or refastenably connecting rear side panels 404, 406 with respective front side panels 408, 410 to define a continuous perimeter waist opening and continuous perimeter leg openings.

Figure 10:
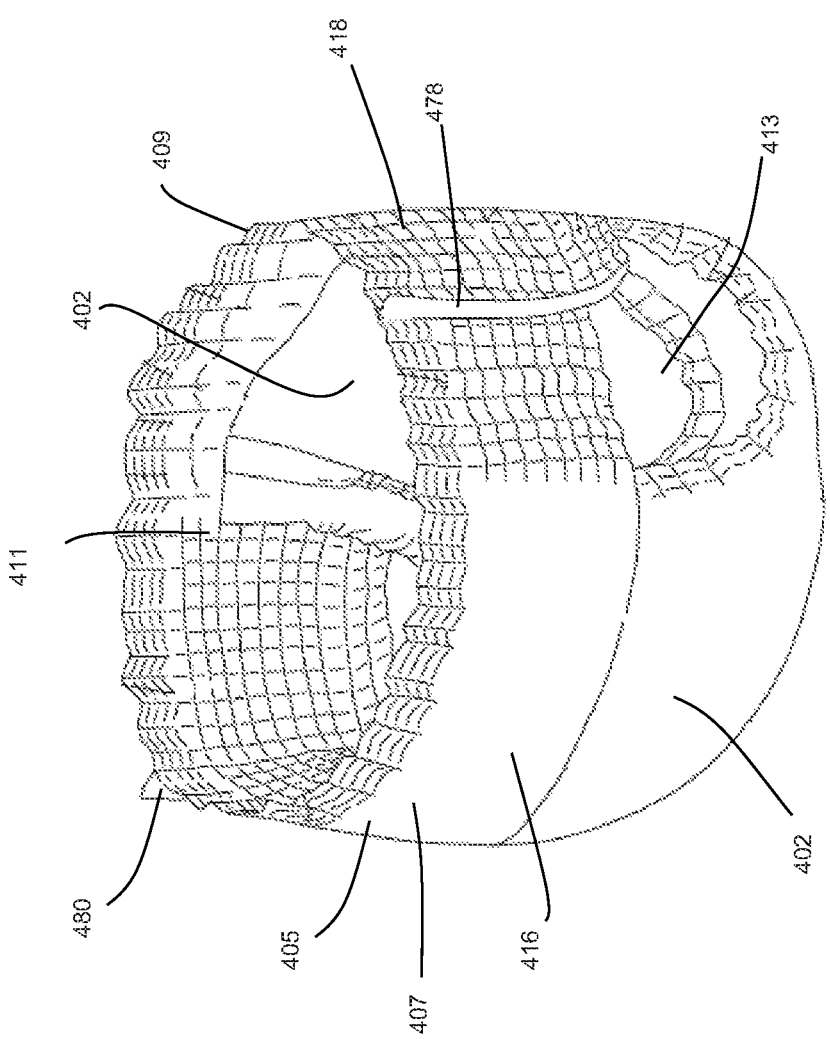
FIG. 10 is a perspective view of a diaper pant.

As shown in FIG. 10, diaper pants may be manufactured with a ring-like elastic belt 405 and provided to consumers in a configuration wherein the front waist region 416 and the back waist region 418 are connected to each other as packaged, prior to being applied to the wearer. As such, diaper pants may have a continuous perimeter waist opening 411 and continuous perimeter leg openings 413 such as shown in FIG. 2. The ring-like elastic belt 405 may be defined by a first elastic belt 407 connected with a second elastic belt 409. FIG. 2 shows a perspective view of an example diaper pant 400 in a pre-fastened configuration including a chassis 402 and a ring-like elastic belt 405, wherein a first elastic belt 407 and a second elastic belt 409 are connected together to form a ring-like elastic belt 405. For example, opposing end regions of the first elastic belt 407 may be connected with the opposing end regions of the second elastic belt 409 at first side seam 478 and second side seam 480.

As described above, the elastic parts 300 discussed herein may be used as to construct various different components used in the manufacture of different types of absorbent articles. For example with reference to FIGS. 9A, 9B, and 10, the elastic parts herein may be used to form all or portions of components such as: chassis 402; side panels 404, 406, 408, 410; belts 407, 409; backsheets 436; topsheets 438; absorbent assembly 440; leg cuffs 456; waistband 458; side flaps 460; fastening members 462, 464; and/or connection zone 468. For example, as shown in FIG. 12, transfer assemblies 100 with carrier surfaces 108 as disclosed herein may be utilized to apply elastic parts in the form of waistbands 458 to a downstream carrier 202 in the form an advancing topsheet 438 substrate. For example, as shown in FIG. 11, transfer assemblies 100 with carrier surfaces 108 as disclosed herein may be utilized to apply elastic parts 300 in the form of chassis 402 to a downstream carrier 202 in the form an advancing first belt 107 and second belt 109.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for transporting a discrete elastic part to a carrier, the method comprising the steps of:
   providing a frame comprising a first axis of rotation;
   providing a transfer member rotatably connected with the frame, the transfer member comprising a carrier surface, a first elongate aperture in the carrier surface, and a second elongate aperture in the carrier surface, the first and second elongate apertures each comprising a side edge and an end edge, wherein the side edge is longer than the end edge;
   rotating the transfer member about the first axis of rotation in a machine direction;
   rotating the carrier surface about a second axis to a first orientation wherein the side edges of the first and second apertures extend generally perpendicular to the machine direction;
   positioning the discrete elastic part in a stretched condition on the carrier surface, wherein the carrier surface is in the first orientation;
   forcing a first portion of the discrete elastic part into the first aperture and a second portion of the discrete elastic part into the second aperture to counteract contraction of the discrete elastic part between the side edge of the first aperture and the side edge of the second aperture;
   rotating the carrier surface of the transfer member and the discrete elastic part about the second axis of rotation to place the carrier surface in a second orientation wherein the side edges of the first and second apertures extend generally parallel to the machine direction; and
   sliding the discrete elastic part over the end edges of the first and second apertures in the carrier surface of the transfer member onto a carrier while the carrier surface is in the second orientation.

2. The method of claim 1, wherein the step of positioning the discrete elastic part in a stretched condition on the carrier surface further comprises the step of advancing a continuous elastic substrate onto the carrier surface of the transfer member and cutting the discrete part from the continuous elastic substrate.

3. The method of claim 1, further comprising the step of advancing the carrier surface of the transfer member at a first speed and advancing the carrier at a second speed adjacent the carrier surface while sliding the discrete part over the end edges of the first and second apertures.

4. The method of claim 3, wherein the second speed is greater than the first speed.

5. The method of claim 1, wherein the step of forcing a first portion of the discrete elastic part into the first aperture further comprises the step of applying a vacuum pressure to the first aperture.

6. The method of claim 1, wherein the side edge of the first aperture is straight.

7. The method of claim 1, wherein the end edge of the first aperture is curved.

8. The method of claim 1, wherein the end edge of the first aperture is chamfered.

9. The method of claim 1, wherein a ratio of a length of the side edge to a length of the end edge is equal to or greater than about 6.

10. The method of claim 1, wherein the carrier comprises an advancing substrate.

11. A method for transporting a discrete part to a carrier, the method comprising the steps of:
    providing a transfer member comprising a carrier surface, a first elongate aperture in the carrier surface, and a second elongate aperture in the carrier surface, the first and second elongate apertures each comprising a perimeter defining a maximum width W and a maximum length L, wherein the maximum length L is greater than the maximum width W, and
    advancing the transfer member in a machine direction;
    positioning a discrete part in a stretched condition on the carrier surface of the transfer member while the carrier surface is in a first orientation wherein the maximum widths W of the first and second elongate apertures extend generally parallel to the machine direction;
    forcing a first portion of the discrete part into the first aperture and a second portion of the discrete part into the second aperture to counteract contraction of the discrete part between the first aperture and the second aperture;
    rotating the discrete part and the carrier surface about a first axis to place the carrier surface in a second orientation wherein the maximum length L of the elongate aperture extends generally parallel to the machine direction; and
    transferring the discrete part from the carrier surface of the transfer member to a carrier while the carrier surface of the transfer member is in the second orientation.

12. The method of claim 11, wherein the step of advancing the transfer member further comprises the step of rotating the transfer member about a second axis.

13. The method of claim 11, wherein the perimeter of the first aperture comprises first and second opposing side edges and first and second opposing end edges, wherein the first and second side edges are longer than the first and second end edges.

14. The method of claim 13, wherein the first and second end edges are curved and the wherein the first and second side edges are straight.

15. The method of claim 11, wherein a ratio of the maximum length L of the first aperture to the maximum width of the first aperture is equal to or greater than about 6.

16. The method of claim 11, wherein the step of positioning the discrete part in a stretched condition on the carrier surface further comprises the step of advancing a continuous substrate onto the carrier surface of the transfer member and cutting the discrete part from the continuous substrate.

17. The method of claim 11, wherein the step of transferring the discrete part from the carrier surface further comprises advancing the carrier surface of the transfer member at a first speed and advancing the carrier at a second speed, wherein the second speed is greater than the first speed.

* * * * *